(12) United States Patent
Lorenzo

(10) Patent No.: US 8,920,459 B2
(45) Date of Patent: Dec. 30, 2014

(54) EMBOLIC COIL DETACHMENT MECHANISM WITH FLEXIBLE DISTAL MEMBER AND RESISTIVE ELECTRICAL HEATING ELEMENT

(75) Inventor: Juan A. Lorenzo, Davie, FL (US)

(73) Assignee: DePuy Synthes Products, LLC, Raynham, MA (US)

(*) Notice: Subject to any disclaimer, the term of this patent is extended or adjusted under 35 U.S.C. 154(b) by 314 days.

(21) Appl. No.: 13/436,430

(22) Filed: Mar. 30, 2012

(65) Prior Publication Data

US 2013/0261713 A1 Oct. 3, 2013

(51) Int. Cl.
*A61M 29/00* (2006.01)

(52) U.S. Cl.
USPC .......................................... 606/200; 607/113

(58) Field of Classification Search
USPC ........................ 606/200, 108, 194; 607/113
See application file for complete search history.

(56) References Cited

U.S. PATENT DOCUMENTS

| | | | |
|---|---|---|---|
| 5,578,074 A | 11/1996 | Mirigian | |
| 5,911,737 A | 6/1999 | Lee et al. | |
| 5,989,242 A | 11/1999 | Saadat et al. | |
| 6,059,815 A | 5/2000 | Lee et al. | |
| 6,102,933 A | 8/2000 | Lee et al. | |
| 6,224,610 B1 | 5/2001 | Ferrera | |
| 6,296,622 B1 | 10/2001 | Kurz et al. | |
| 6,589,236 B2 * | 7/2003 | Wheelock et al. | 606/32 |
| 6,743,236 B2 | 6/2004 | Barry et al. | |
| 7,578,826 B2 | 8/2009 | Gandhi et al. | |
| 7,582,101 B2 | 9/2009 | Jones et al. | |
| 7,591,833 B2 | 9/2009 | Jones et al. | |
| 7,744,604 B2 | 6/2010 | Maitland et al. | |
| 7,776,054 B2 | 8/2010 | Gandhi et al. | |
| 7,780,680 B2 | 8/2010 | Gandhi et al. | |
| 7,972,342 B2 * | 7/2011 | Gandhi et al. | 606/108 |
| 2001/0029352 A1 | 10/2001 | Gandhi et al. | |
| 2006/0025801 A1 | 2/2006 | Lulo et al. | |
| 2009/0177261 A1 * | 7/2009 | Teoh et al. | 623/1.11 |

FOREIGN PATENT DOCUMENTS

WO 0158366 A1 8/2001

OTHER PUBLICATIONS

EPO, European Search Report from European Patent Application No. EP13162034 dated Jul. 24, 2013.

* cited by examiner

*Primary Examiner* — Kathleen Holwerda
*Assistant Examiner* — Sarah Simpson

(57) ABSTRACT

An embolic coil detachment system includes an elongated, flexible polymer tube having a tubular wall with an inner surface defining an interior lumen. A distal portion of the tubular wall has a score line, and a resistive heating element is located near the score line and in immediate contact with a surface of a distal portion of the tubular wall, to provide direct heating of the distal portion of the flexible polymer tube adjacent to the score line. A therapeutic embolic coil includes a headpiece that is releasably attached within the distal portion of the flexible polymer tube, and that is releasable by heating of the distal portion of the tubular shaft to cause the distal portion of the tubular wall to split along the score line.

18 Claims, 6 Drawing Sheets

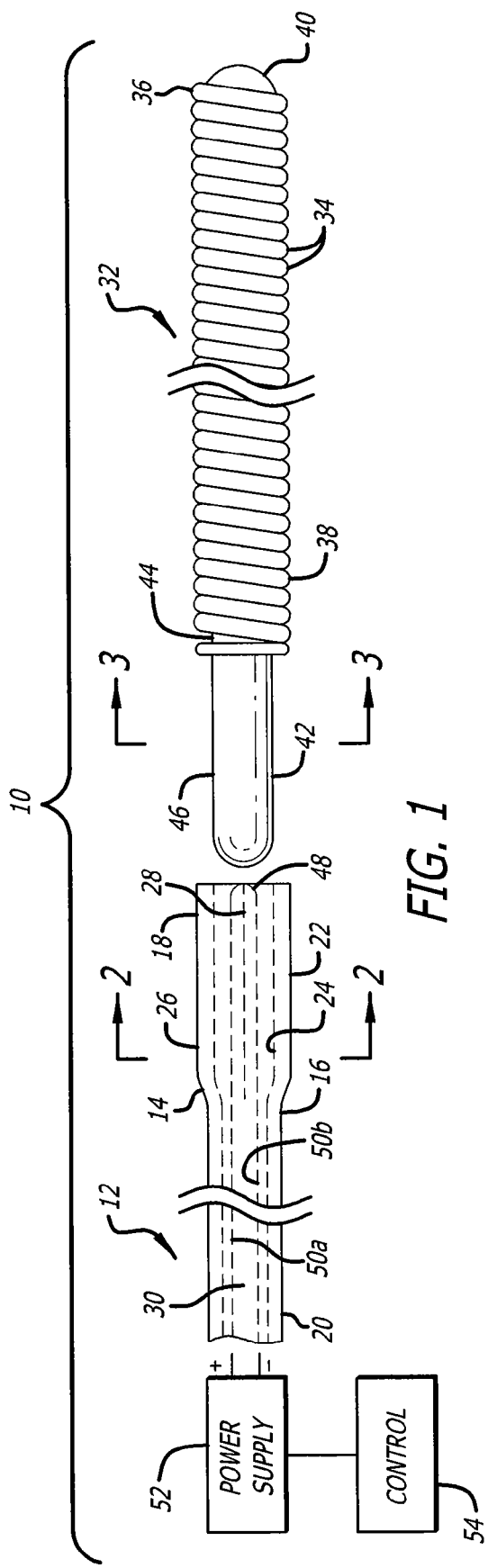

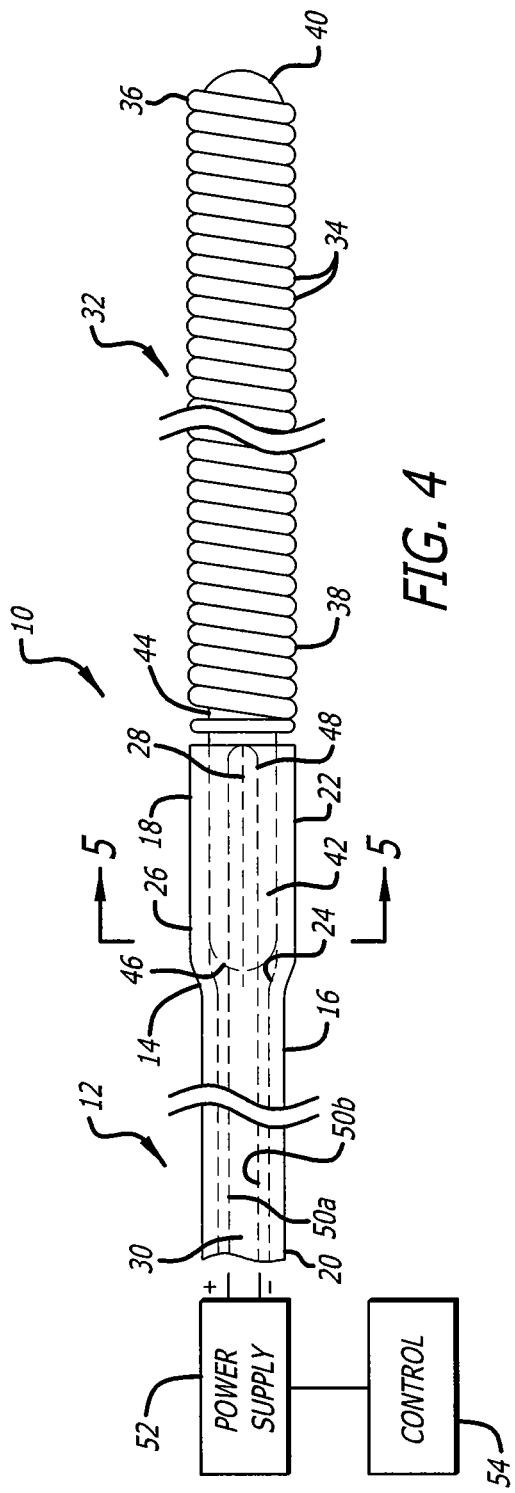
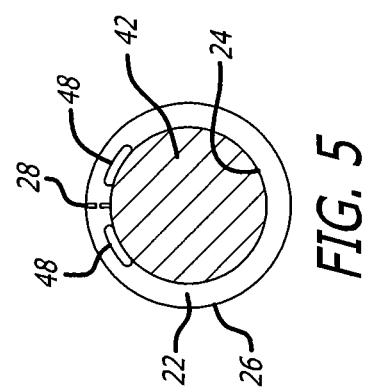

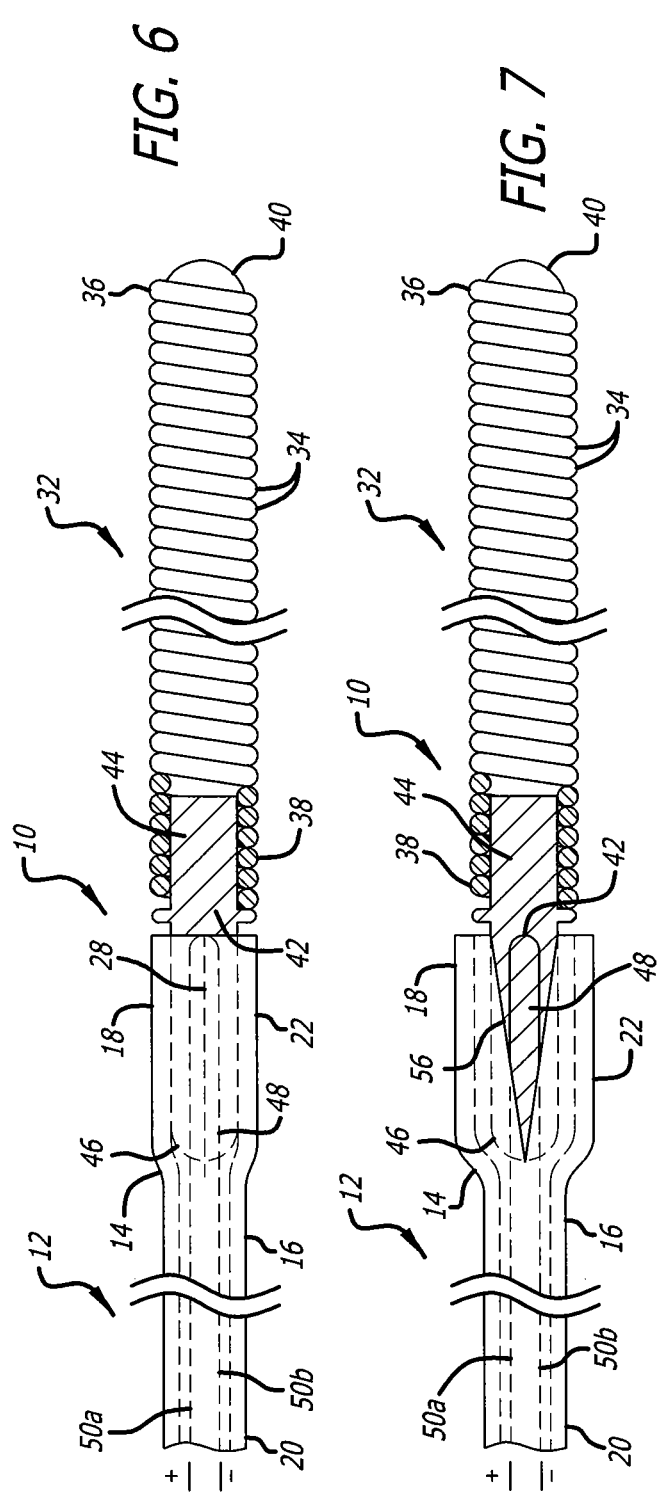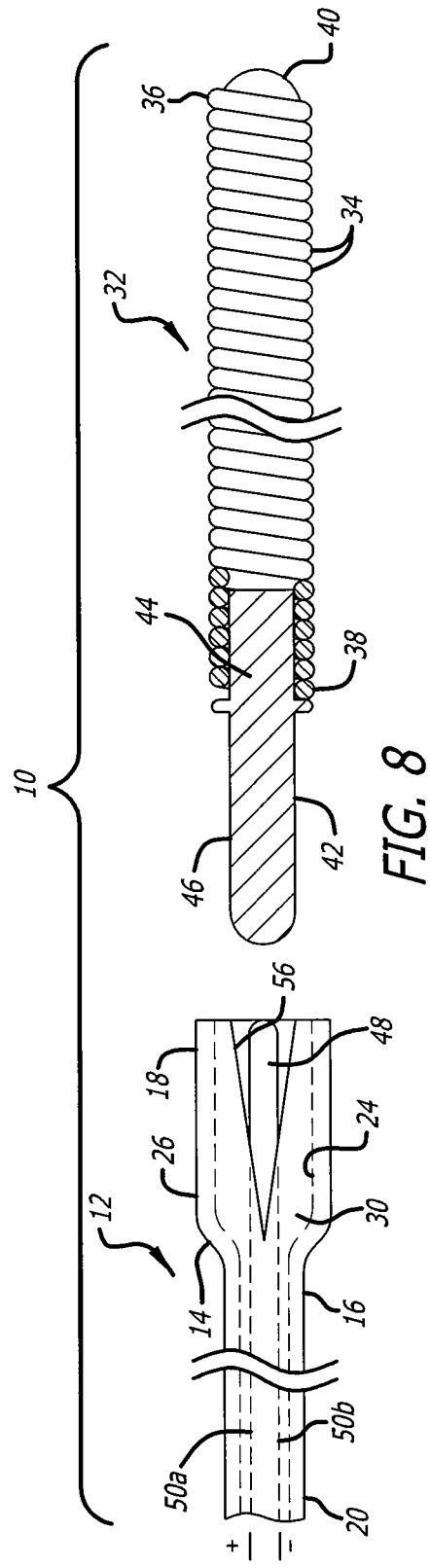

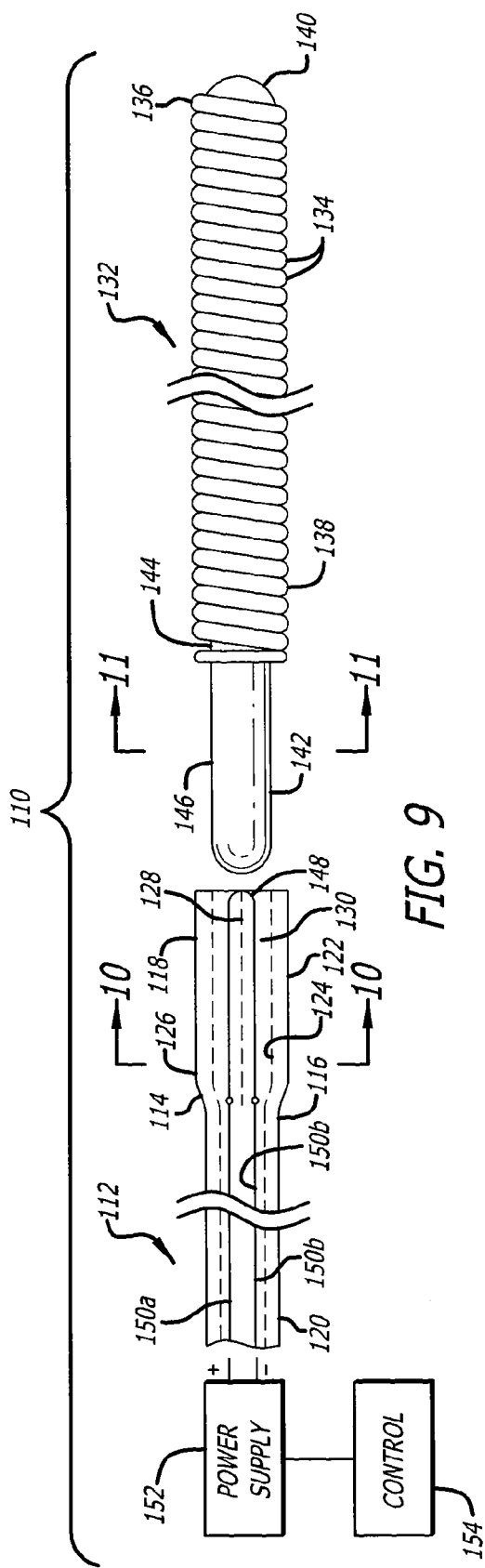
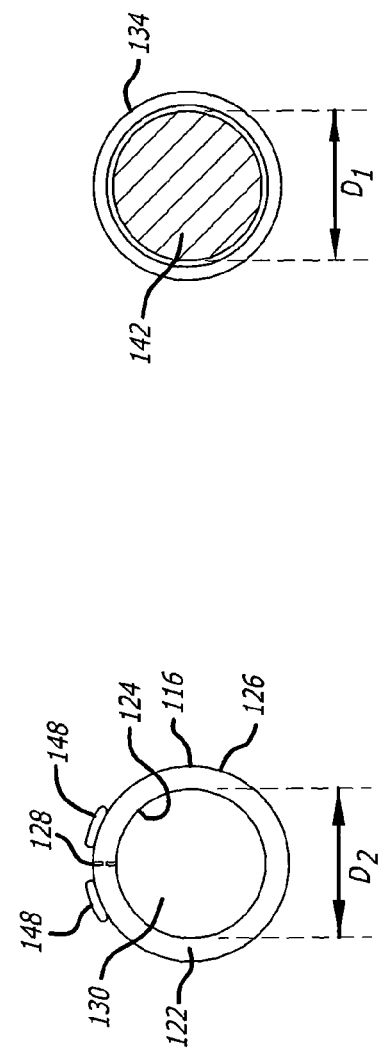

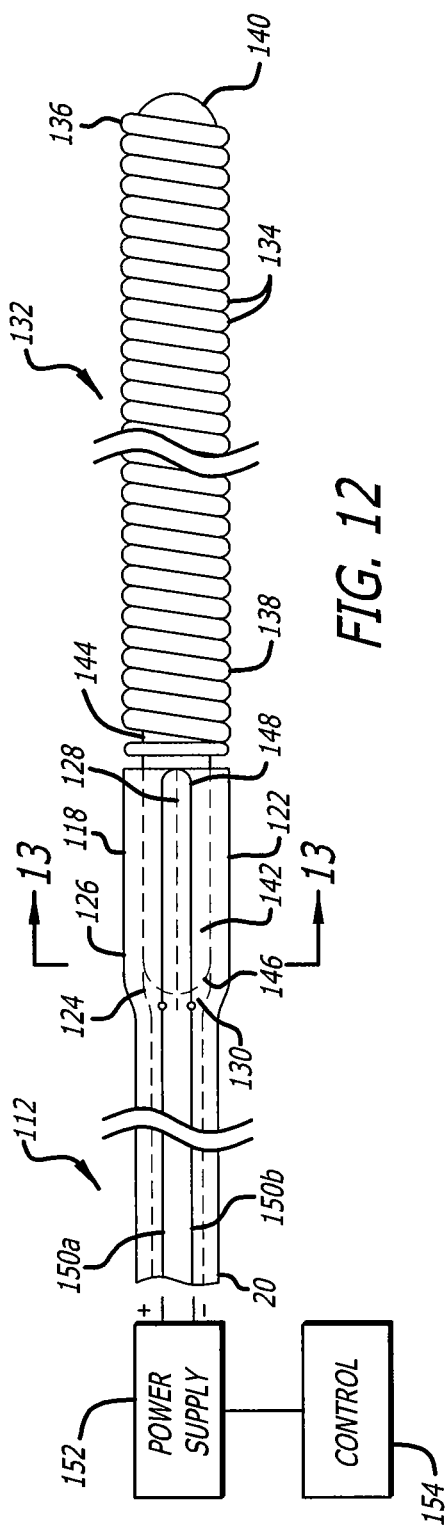
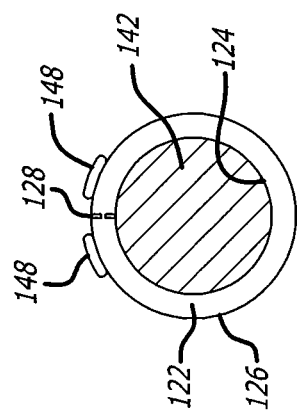
FIG. 12
FIG. 13

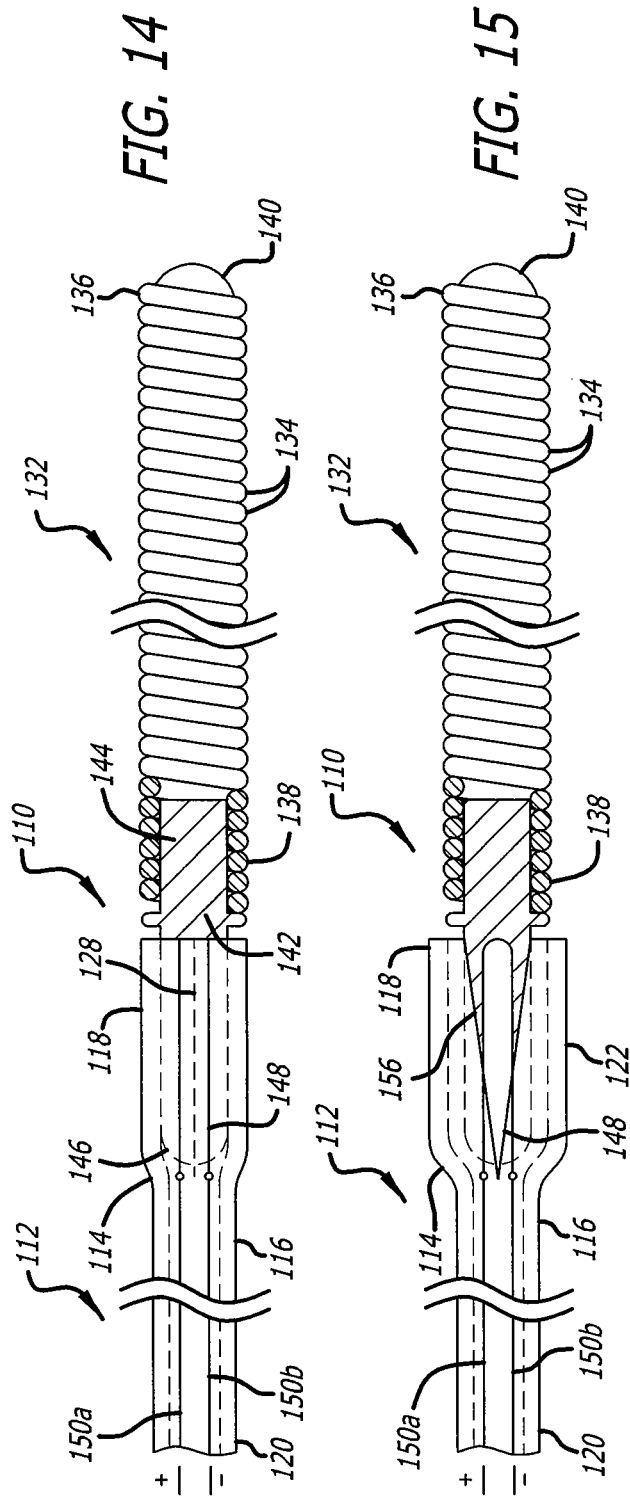
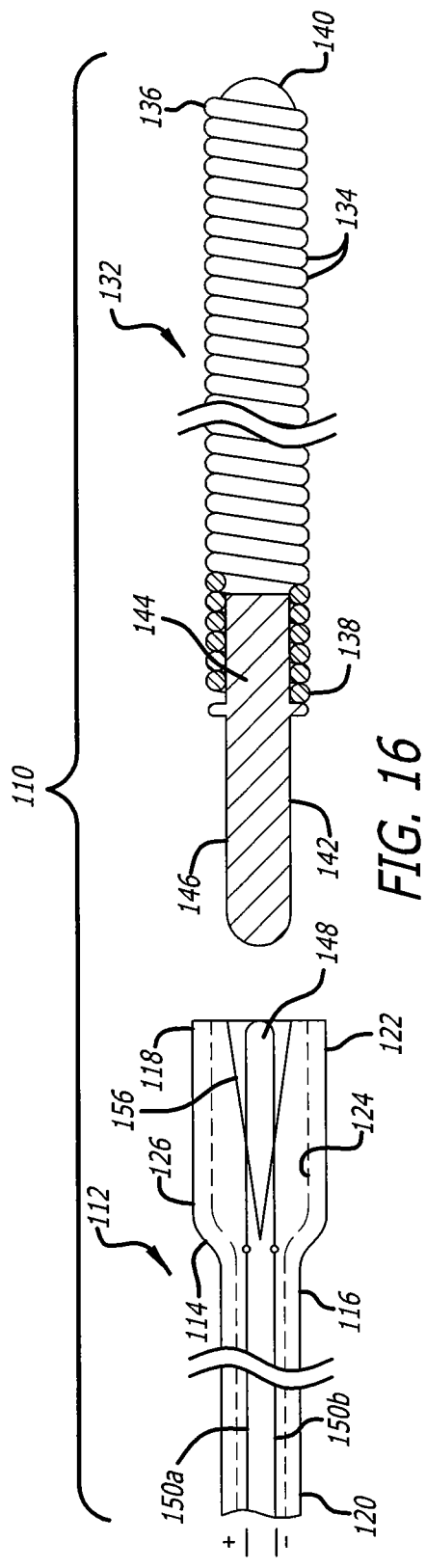

EMBOLIC COIL DETACHMENT MECHANISM WITH FLEXIBLE DISTAL MEMBER AND RESISTIVE ELECTRICAL HEATING ELEMENT

BACKGROUND OF THE INVENTION

This invention relates generally to devices for interventional therapeutic treatment or vascular surgery for treatment of defects in the vasculature, and more particularly concerns a system and method for delivering an embolic coil to a treatment site in a vasculature of a patient, such as for treatment of aneurysms.

Aneurysms have been treated with external surgically placed clips, detachable vasoocclusive balloons and embolus generating vasoocclusive devices such as one or more vasoocclusive coils, which are typically either placed within a blood vessel to block the flow of blood through a vessel making up that portion of the vasculature through the formation of an embolus, or are placed within an aneurysm stemming from the vessel to form such an embolus within the aneurysm. Delivery of one or more of such vasoocclusive coils has typically been accomplished by pushing them through a catheter to the target site.

In one conventional technique, a conductive guidewire delivers a high frequency current through the guidewire to melt and sever a joint to detach an implanted device from the guidewire. The patient is grounded during the procedure, and current is introduced via the guidewire, rather than with a two way current path.

Another device is known in which a device to be implanted is detached by application of a high-frequency current which melts and severs a resin that is used to retain the device to be implanted until the device is to be deployed. In another known device, an electrolytically severable link is dissolved by activation of a power source electrically coupled to the electrolytically severable link to detach the device to be implanted.

An apparatus for deployment of a micro-coil is also known in which the micro-coil is detachably mounted to the distal portion of a pusher by a tubular collar that can be heated by an electrical resistance coil to expand the collar and release and deploy the therapeutic device.

In order to allow delivery and withdrawal of embolic coils, one known implant delivery assembly utilizes a shape memory decoupling mechanism activated when exposed to body temperature. A cooling solution is flushed through the catheter during introduction and placement of the implant in order to prevent premature release of the implant prior to the time that the implant is to be released. Another implant delivery assembly includes an electrical heating system for heating the coupling mechanism to a temperature at which the shape memory material returns to its original shape, to deploy the implant.

A thermally activated occlusive implant delivery system is also known in which a pusher includes a distal coupling formed of shape memory material having different configurations dependent upon temperature, that interlocks with the implant in one configuration and that releases the implant in another configuration.

In another device for releasing an embolic coil inside an aneurysm, a coupling made of a shape memory alloy is responsive to a change in temperature beyond a predetermined transformation point so as to change the shape of the coupling from a first configuration, in which the coupling receives and holds the proximal end of the coil, to a second configuration in which the coil can be released from the coupling. An energy receiver is used to heat the coupling to a temperature above the transformation point with laser or electrical energy received from an external source.

There is a need for an improved apparatus for deploying therapeutic interventional devices with a strategically placed heating element that provides direct heating of a flexible polymer coupling releasably retaining an embolic coil for delivery when the heating element is energized. The present invention meets these and other needs.

SUMMARY OF THE INVENTION

Briefly and in general terms, the present invention provides for a detachment system and method for delivering an embolic coil to a treatment site in a vasculature of a patient, utilizing a resistive heating element disposed longitudinally along and in immediate contact with a tubular wall surface of a distal portion of the flexible polymer tube adjacent to a score line in the tubular wall surface, to provide direct heating of the distal portion of the flexible polymer tube to cause the flexible polymer tube to split along the score line, to thereby release the embolic coil when the resistive heating element is energized.

The present invention accordingly provides for a detachment system for delivering embolic coils to a treatment site in a vasculature of a patient, including an elongated, flexible polymer tube having a distal portion and a proximal portion. The flexible polymer tube has a tubular wall with an inner surface, an outer surface and a first thickness, and the inner surface of the tubular wall defining an interior lumen extending through the flexible polymer tube between the distal and proximal portions of the flexible polymer tube. In a presently preferred aspect, the distal portion of the tubular wall of the flexible polymer tube has a score line formed in at least one of the inner surface and the outer surface of the tubular wall, and having a second thickness that is less than the first thickness.

A resistive heating element is located adjacent to the score line and in immediate contact with and extending longitudinally along at least one of the inner surface and the outer surface of the tubular wall of the distal portion of the flexible polymer tube. The resistive heating element is preferably configured to provide direct heating of the distal portion of the flexible polymer tube adjacent to the score line when the resistive heating element is energized.

A therapeutic embolic coil is releasably mounted to the distal portion of the flexible polymer tube, and includes a headpiece or stem, a distal portion of which is attached to a proximal end of the embolic coil. A proximal portion of the headpiece is releasably attached within the distal portion of the flexible polymer tube, and is releasable from the distal portion of the tubular wall by heating of the distal portion of the tubular shaft, to cause the distal portion of the tubular wall to split along the score line, to thereby release the headpiece of the therapeutic embolic coil from the flexible polymer tube.

In a presently preferred aspect, the therapeutic embolic coil is a helical embolic coil. In another presently preferred aspect, the therapeutic embolic coil includes a rounded distal tip attached to the distal end of the embolic coil. In another presently preferred aspect, the proximal portion of the headpiece has a generally cylindrical configuration, and extends proximally of the proximal portion of the embolic coil.

In another presently preferred aspect, the resistive heating element is disposed longitudinally along and in immediate contact with the inner surface of the distal portion of the flexible polymer tube, although the resistive heating element can alternatively be disposed longitudinally along and in immediate contact with the outer surface of the distal portion of the flexible polymer tube. In another presently preferred aspect, the resistive heating element is disposed longitudinally beside the score line. In another presently preferred aspect, when the resistive heating element is disposed longitudinally along and in immediate contact with the inner surface of the distal portion of the flexible polymer tube, two electrical conductors extend through the interior lumen of the elongated, flexible polymer tube and are electrically connected to the resistive heating element; and when the resistive heating element can alternatively be disposed longitudinally along and in immediate contact with the outer surface of the distal portion of the flexible polymer tube, two electrical conductors extend along the outer surface of the elongated, flexible polymer tube and are electrically connected to the resistive heating element.

These and other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1 is a partial sectional schematic diagram of a pusher member and embolic coil of a first embodiment of the detachment system of the present invention.

FIG. 2 is a cross-sectional view of the distal portion of the pusher member of the detachment system taken along line 2-2 of FIG. 1.

FIG. 3 is a cross-sectional view of the headpiece of the embolic coil of the detachment system taken along line 3-3 of FIG. 1.

FIG. 4 is a partial sectional schematic diagram of the pusher member and embolic coil of the detachment system of FIG. 1 joined together.

FIG. 5 is a cross-sectional view taken along line 5-5 of FIG. 4.

FIG. 6 is a partial sectional schematic diagram of the pusher member and embolic coil of the detachment system of FIG. 1 joined together, prior to activation of the resistive heating element.

FIG. 7 is a partial sectional schematic diagram similar to FIG. 6, illustrating activation of the resistive heating element to splitting of the distal portion of the flexible polymer tube.

FIG. 8 is a partial sectional schematic diagram similar to FIG. 6, illustrating release of the headpiece and embolic coil.

FIG. 9 is a partial sectional schematic diagram of a pusher member and embolic coil of a second embodiment of the detachment system of the present invention.

FIG. 10 is a cross-sectional view of the distal portion of the pusher member of the detachment system taken along line 10-10 of FIG. 9.

FIG. 11 is a cross-sectional view of the headpiece of the embolic coil of the detachment system taken along line 11-11 of FIG. 9.

FIG. 12 is a partial sectional schematic diagram of the pusher member and embolic coil of the detachment system of FIG. 9 joined together.

FIG. 13 is a cross-sectional view taken along line 13-13 of FIG. 12.

FIG. 14 is a partial sectional schematic diagram of the pusher member and embolic coil of the detachment system of FIG. 9 joined together, prior to activation of the resistive heating element.

FIG. 15 is a partial sectional schematic diagram similar to FIG. 14, illustrating activation of the resistive heating element to splitting of the distal portion of the flexible polymer tube.

FIG. 16 is a partial sectional schematic diagram similar to FIG. 14, illustrating release of the headpiece and embolic coil.

DETAILED DESCRIPTION OF THE PREFERRED EMBODIMENTS

Referring to the drawings, which are provided by way of example, and not by way of limitation, in a first embodiment, the present invention provides for a detachment system 10 for delivering embolic coils to a treatment site in a vasculature of a patient, as is illustrated in FIGS. 1-8. The detachment system includes an elongated, flexible pusher member 12 having a distal portion 14 formed from a flexible polymer tube 16 having a distal portion 18 for release and deployment of a therapeutic embolic coil, and a proximal portion 20. The distal portion of the flexible polymer tube has a tubular wall 22 with an inner tubular wall surface 24 and an outer tubular wall surface 26, and a score line 28 is formed in at least one of the inner surface and the outer surface of the distal portion of the flexible distal polymer tube in the area where the heating element is located, as will be described later. The tubular wall of the flexible polymer tube has a first thickness, and the portion or portions of the tubular wall where the score line is formed has a second thickness that is less than the first thickness. The score line typically can be made with a laser or mechanically such as by inscribing the tubular wall with one or more superficial cuts, although the score line may also be formed by etching, molding, or any other similar suitable manner, and may be formed by one or more sequences of perforations extending partially through or completely through the tubular wall, to form a thinned or otherwise weakened line along which the tubular wall will split when the tubular wall is expanded. The flexible polymer tube tubular wall also defines an interior lumen 30 extending through the elongated, flexible polymer tube between the distal and proximal portions of the flexible polymer tube.

The therapeutic embolic coil 32 in one presently preferred aspect includes helical coils 34, and typically has a distal end 36 and a proximal end 38, and typically includes a rounded distal tip 40 attached to the distal end of the embolic coil, such as by solder, welding or adhesive, for example. The therapeutic embolic coil also preferably includes a headpiece or stem 42 having a distal portion 44 and a proximal portion 46. The therapeutic embolic coil is typically released within the vasculature of a patient, introduced through a delivery catheter (not shown), for treatment of a portion of a patient's vasculature, such as an aneurysm. In one presently preferred aspect, the headpiece or stem has a generally cylindrical configuration. The distal portion of the headpiece or stem is typically attached to the proximal end of the embolic coil, such as by solder, welding or adhesive, for example, leaving the proximal portion of the headpiece or stem extending proximally of the proximal portion of the embolic coil.

A resistive heating element 48 advantageously is disposed longitudinally along and in immediate contact with the inner tubular wall surface of the tubular wall of the distal portion of the flexible polymer tube, and preferably straddles, or extends beside or on either side of the score line, to provide direct heating of the distal portion of the flexible polymer tube adjacent to the score line when the resistive heating element is energized. Two electrical conductors 50a, 50b extend through the interior lumen of the flexible polymer tube from a proximal portion of the flexible polymer tube to the resistive heating element, and are operatively electrically connected between the resistive heating element and a power supply 52, which can in turn be operated by a control unit 54. Alternatively, the power supply and control unit may optionally be combined. The resistive heating element can be fabricated from platinum, stainless steel, or other high resistance materials, and the electrical connectors can be copper or other highly electrically conductive leads, for example. The power supply can be operated to supply electrical current to the resistive heating element to heat the distal portion of the flexible polymer tube to cause the distal portion of the flexible polymer tube to expand and release the therapeutic helical embolic coil, as is illustrated in FIGS. 6-8.

Referring to FIGS. 1, 4 and 5, the therapeutic helical embolic coil is releasably mounted to the distal portion of the flexible polymer tube by inserting the proximal portion of the headpiece or stem into the distal portion of the flexible polymer tube, with the resistive heating element disposed between the inner wall surface of the tubular wall of the distal portion of the flexible polymer tube and the proximal portion of the headpiece or stem. Referring to FIGS. 2 and 3, the embolic coil headpiece or stem preferably has an outer diameter $D_1$ larger than an inner diameter $D_2$ of the lumen at the distal portion of the flexible shape memory polymer tubing, thus creating an interference fit between the embolic coil headpiece or stem and the distal portion of the flexible polymer tubing inner diameter. This dimensional interference prevents the premature separation between the embolic coil and the tube and the outer diameter of the embolic coil headpiece. To detach the embolic coil, electrical current is applied to the heating element in order to raise the temperature of the heating element and cause a split or splitting 56 of the distal end of the polymer tube along the score line to thereby release the embolic coil.

In a second embodiment, the present invention provides for a detachment system 110 for delivering embolic coils to a treatment site in a vasculature of a patient, as is illustrated in FIGS. 9-16. The detachment system includes an elongated, flexible pusher member 112 having a distal portion 114 formed from a flexible polymer tube 116 having a distal portion 118 for release and deployment of a therapeutic embolic coil, and a proximal portion 120. The distal portion of the flexible polymer tube has a tubular wall 122 with an inner tubular wall surface 124 and an outer tubular wall surface 126, and a score line 128 is formed in the outer surface of the distal portion of the flexible distal polymer tube in the area where the heating element is located, as will be described later. The tubular wall of the flexible polymer tube has a first thickness, and the portion or portions of the tubular wall where the score line is formed has a second thickness that is less than the first thickness. The score line typically can be made with a laser or mechanically such as by inscribing the tubular wall with one or more superficial cuts, although the score line may also be formed by etching, molding, or any other similar suitable manner, and may be formed by one or more sequences of perforations extending partially through or completely through the tubular wall, to form a thinned or otherwise weakened line along which the tubular wall will split when the tubular wall is expanded. The flexible polymer tube tubular wall defines an interior lumen 130 extending through the elongated, flexible polymer tube between the distal and proximal portions of the flexible polymer tube.

The therapeutic embolic coil 132 in one presently preferred aspect includes helical coils 134, and typically has a distal end 136 and a proximal end 138, and typically includes a rounded distal tip 140 attached to the distal end of the embolic coil, such as by solder, welding or adhesive, for example. The therapeutic embolic coil also preferably includes a headpiece or stem 142 having a distal portion 144 and a proximal portion 146. The therapeutic embolic coil is typically released within the vasculature of a patient, introduced through a delivery catheter (not shown), for treatment of a portion of a patient's vasculature, such as an aneurysm. In one presently preferred aspect, the headpiece or stem has a generally cylindrical configuration. The distal portion of the headpiece or stem is typically attached to the proximal end of the embolic coil, such as by solder, welding or adhesive, for example, leaving the proximal portion of the headpiece or stem extending proximally of the proximal portion of the embolic coil.

A resistive heating element 148 advantageously is disposed longitudinally along and in immediate contact with the outer wall surface of the tubular wall of the distal portion of the flexible polymer tube, and preferably on either side of the score line, to provide direct heating of at least a portion of the length of the distal portion of the flexible polymer tube when the resistive heating element is energized. Two electrical conductors 150*a*, 150*b* extend longitudinally along the outer surface of the flexible polymer tube from a proximal portion of the flexible polymer tube to the resistive heating element, and are operatively electrically connected between the resistive heating element and a power supply 152, which can in turn be operated by a control unit 154. The electrical conductors may optionally extend through the interior lumen of the flexible polymer tube from a proximal portion of the flexible polymer tube, and through the tubular wall to connect with the resistive heating element. The power supply and control unit may optionally be combined. The resistive heating element can be fabricated from platinum, stainless steel, or other high resistance materials, and the electrical connectors can be copper or other highly electrically conductive leads, for example. The power supply can be operated to supply electrical current to the resistive heating element to heat the distal portion of the flexible polymer tube to cause the distal portion of the flexible polymer tube to expand and release the therapeutic helical embolic coil, as is illustrated in FIGS. 14-16.

Referring to FIGS. 9, 12 and 13, the therapeutic helical embolic coil is releasably mounted to the distal portion of the flexible polymer tube by inserting the proximal portion of the headpiece or stem into the distal portion of the flexible polymer tube, with the resistive heating element disposed between the inner wall surface of the tubular wall of the distal portion of the flexible polymer tube and the proximal portion of the headpiece or stem. Referring to FIGS. 10 and 11, the embolic coil headpiece or stem preferably has an outer diameter $D_1$ larger than an inner diameter $D_2$ of the lumen at the distal portion of the flexible shape memory polymer tubing, thus creating an interference fit between the embolic coil headpiece or stem and the distal portion of the flexible polymer tubing inner diameter. This dimensional interference prevents the premature separation between the embolic coil and the tube and the outer diameter of the embolic coil headpiece. To detach the embolic coil, electrical current is applied to the heating element in order to raise the temperature of the heating element and cause a split or splitting 156 of the distal end of the polymer tube along the score line to thereby release the embolic coil.

In the foregoing embodiments, the flexible polymer tube can be formed of a polymer that shrinks or changes shape when heated by the resistive heating element, and can be formed as a mechanically expanded tube formed of a polymer such as polyurethane, nylon, polyolefin, a fluoropolymer such as polytetrafluoroethylene (PTFE), polyvinylidene fluoride (PVDF), fluorinated ethylene propylene (FEP), polyvinyl chloride (PVC), neoprene, silicone elastomer, or synthetic rubber, or combinations thereof, for example, or other similar suitable flexible polymers or thermoplastics that shrink or change shape when heated.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A detachment system for delivering embolic coils to a treatment site in a vasculature of a patient, comprising:
   an elongated, flexible polymer tube having a distal portion and a proximal portion, said polymer tube having a tubular wall with an inner surface, an outer surface and a first thickness, said distal portion of said tubular wall of said flexible polymer tube having a score line formed in at least one of said inner surface and said outer surface of said tubular wall, said score line having a second thickness that is less than said first thickness, said inner surface of said tubular wall defining an interior lumen extending through said flexible polymer tube between said distal and proximal portions of the flexible polymer tube;
   a resistive heating element in immediate contact with and extending longitudinally along at least one of said inner surface and said outer surface of said tubular wall of said distal portion of said flexible polymer tube, said resistive heating element being disposed longitudinally beside said score line, and said resistive heating element being configured to provide direct heating of the distal portion of the flexible polymer tube adjacent to said score line when the resistive heating element is energized; and
   a therapeutic embolic coil releasably mounted to the distal portion of said flexible polymer tube, said embolic coil having a distal end and a proximal end, said therapeutic embolic coil including a headpiece having a distal portion and a proximal portion, the distal portion of the headpiece being attached to the proximal end of the embolic coil, and the proximal portion of the headpiece being releasably attached within said interior lumen in said elongated, flexible polymer tube within said distal portion of said flexible polymer tube, said proximal portion of the headpiece being releasable from said distal portion of said tubular wall by heating of said distal portion of the tubular shaft to cause said distal portion of the tubular wall to split along said score line to release said headpiece of said therapeutic embolic coil from said flexible polymer tube.

2. The detachment system of claim 1, wherein said resistive heating element is disposed longitudinally along and in immediate contact with said inner surface of the distal portion of the flexible polymer tube.

3. The detachment system of claim 1, wherein said resistive heating element is disposed longitudinally along and in immediate contact with said outer surface of the distal portion of the flexible polymer tube.

4. The detachment system of claim 2, further comprising two electrical conductors extending through the interior lumen of the flexible polymer tube and electrically connected to the resistive heating element.

5. The detachment system of claim 3, further comprising two electrical conductors extending longitudinally along the outer surface of the flexible polymer tube and electrically connected to the resistive heating element.

6. The detachment system of claim 1, wherein said therapeutic embolic coil comprises a helical embolic coil.

7. The detachment system of claim 1, wherein said proximal portion of said headpiece has a generally cylindrical configuration.

8. The detachment system of claim 1, wherein said proximal portion of the headpiece extends proximally of said proximal portion of the embolic coil.

9. The detachment system of claim 1, wherein said therapeutic embolic coil includes a rounded distal tip attached to said distal end of said embolic coil.

10. A detachment system for delivering embolic coils to a treatment site in a vasculature of a patient, comprising:
    an elongated, flexible polymer tube having a distal portion and a proximal portion, said polymer tube having a tubular wall with an inner surface, an outer surface and a first thickness, said inner surface of said tubular wall defining an interior lumen extending through said flexible polymer tube between said distal and proximal portions of the flexible polymer tube;
    a resistive heating element disposed in an area of said distal portion of the flexible distal polymer tube in immediate contact with and extending longitudinally along at least one of said inner surface and said outer surface of said tubular wall of said distal portion of said flexible polymer tube, said resistive heating element being configured to provide direct heating of the distal portion of the flexible polymer tube when the resistive heating element is energized, said distal portion of said tubular wall of said flexible polymer tube having a score line formed in at least one of said inner surface and said outer surface of said tubular wall, said score line having a second thickness that is less than said first thickness, said score line being defined in at least one of said inner surface and said outer surface of said distal portion of the flexible distal polymer tube in said area of said distal portion of the flexible distal polymer tube where the heating element is located, and said resistive heating element extending longitudinally on either side of said score line; and
    a therapeutic embolic coil releasably mounted to the distal portion of said flexible polymer tube, said embolic coil having a distal end and a proximal end, said therapeutic embolic coil including a headpiece having a distal portion and a proximal portion, the distal portion of the headpiece being attached to the proximal end of the embolic coil, and the proximal portion of the headpiece being releasably attached within said interior lumen in said elongated, flexible polymer tube within said distal portion of said flexible polymer tube, said proximal portion of the headpiece being releasable from said distal portion of said tubular wall by heating of said distal portion of the tubular shaft to cause said distal portion of the tubular wall to split along said score line to release said headpiece of said therapeutic embolic coil from said flexible polymer tube.

11. The detachment system of claim 10, wherein said resistive heating element is disposed longitudinally along and in immediate contact with said inner surface of the distal portion of the flexible polymer tube.

12. The detachment system of claim 10, wherein said resistive heating element is disposed longitudinally along and in immediate contact with said outer surface of the distal portion of the flexible polymer tube.

13. The detachment system of claim 11, further comprising two electrical conductors extending through the interior lumen of the flexible polymer tube and electrically connected to the resistive heating element.

14. The detachment system of claim 12, further comprising two electrical conductors extending longitudinally along the outer surface of the flexible polymer tube and electrically connected to the resistive heating element.

15. The detachment system of claim 10, wherein said therapeutic embolic coil comprises a helical embolic coil.

16. The detachment system of claim 10, wherein said proximal portion of said headpiece has a generally cylindrical configuration.

17. The detachment system of claim 10, wherein said proximal portion of the headpiece extends proximally of said proximal portion of the embolic coil.

18. The detachment system of claim 10, wherein said therapeutic embolic coil includes a rounded distal tip attached to said distal end of said embolic coil.

* * * * *